(12) United States Patent
Chawla (10) Patent No.: US 6,418,926 B1
(45) Date of Patent: Jul. 16, 2002

(54) MEDICAMENT DELIVERY AND PACKAGING

(75) Inventor: Brindra Paul Singh Chawla, Nottingham (GB)

(73) Assignee: Custom Focus Limited (GB)

( * ) Notice: Subject to any disclaimer, the term of this patent is extended or adjusted under 35 U.S.C. 154(b) by 0 days.

(21) Appl. No.: 09/319,754

(22) PCT Filed: Dec. 17, 1997

(86) PCT No.: PCT/GB97/03478

§ 371 (c)(1),
(2), (4) Date: Oct. 4, 1999

(87) PCT Pub. No.: WO98/26828

PCT Pub. Date: Jun. 25, 1998

(30) Foreign Application Priority Data

Dec. 18, 1996 (GB) ............................................... 9626233

(51) Int. Cl.[7] ............................................... A61M 15/00
(52) U.S. Cl. ................................ 128/203.12; 128/203.15
(58) Field of Search ...................... 128/203.12, 203.15, 128/203.21, 204.13, 204.14

(56) References Cited

U.S. PATENT DOCUMENTS

| | | | | | |
|---|---|---|---|---|---|
| 2,470,296 A | * | 5/1949 | Fields | ........................... | 128/266 |
| 2,534,636 A | * | 12/1950 | Stirn | ........................... | 128/206 |
| 2,642,063 A | * | 6/1953 | Brown | ................... | 128/203.12 |
| 4,570,630 A | * | 2/1986 | Elliott et al. | ........... | 128/203.15 |
| 4,841,964 A | * | 6/1989 | Hurka et al. | ........... | 128/203.15 |
| 5,522,383 A | * | 6/1996 | Calvert et al. | ......... | 128/203.15 |
| 5,778,873 A | * | 7/1998 | Braithwaite | ............ | 128/203.15 |
| 5,797,391 A | * | 8/1998 | Cook et al. | ............. | 128/203.15 |
| 5,823,182 A | * | 10/1998 | Van Oort | ............... | 128/203.12 |
| 5,873,360 A | * | 2/1999 | Davies et al. | .......... | 128/203.15 |
| 5,896,855 A | * | 4/1999 | Hobbs et al. | .......... | 128/203.15 |
| 6,089,227 A | * | 7/2000 | Nilsson | .................. | 128/203.15 |
| 6,230,707 B1 | * | 5/2001 | Horlin | .................... | 128/203.15 |

FOREIGN PATENT DOCUMENTS

| | | | | | |
|---|---|---|---|---|---|
| EP | 0254394 | * | 1/1988 | ............ | 128/203.15 |
| GB | 2253200 | * | 2/1992 | ............ | 128/203.15 |
| GB | WO 94/19041 | * | 9/1994 | ............ | 128/203.15 |

* cited by examiner

Primary Examiner—John G. Weiss
Assistant Examiner—Teena Mitchell
(74) Attorney, Agent, or Firm—Nixon Peabody LLP (57) ABSTRACT

A system for the administration of a powdered medicament by inhalation comprises a container (21) containing a unit dose of medicament in powder form, and a device (10) having a chamber (16) adapted to receive the container (21). The device (10) has air inlets (19, 20) by which air may be drawn into the chamber (16) and a mouthpiece (14) by which air and entrained medicament may be drawn out of the chamber (16). The chamber (16) is substantially circular or annular in form and, in use, the container (21) follows an orbital path within the chamber (16), medicament being dispensed from the container (21) through at least one opening in the container (21). Also described are novel forms of packaging for powdered medicaments which are particularly suitable for use in the system.

52 Claims, 10 Drawing Sheets

MEDICAMENT DELIVERY AND PACKAGING

FIELD OF THE INVENTION

This invention relates to delivery devices and packaging for medicaments, in particular to delivery devices and packaging for the administration of medicaments by inhalation.

BACKGROUND OF THE INVENTION

The administration of powdered medicaments by inhalation is well-established. One form of delivery device which is employed for this purpose is the pressurised aerosol or metered dose inhaler (MDI). MDI's are, however, not suitable for use by all patients, eg small children, or for the administration of all medicaments. Also, there is concern about environmental damage caused by the propellants employed in MDI's. A widely-used alternative is the so-called dry powder inhaler in which medicament powder is dispensed from an elongate gelatine capsule, by causing the capsule to rotate and/or vibrate, into an airstream which is inhaled by the patient. The capsules are pierced. usually at each end. The piercing is carried out in the device by a suitable puncturing mechanism, and it has also been proposed for the capsules to be supplied in pre-pierced form, in packaging which prevents loss of powder from the capsule and the ingress of moisture.

Gelatine capsules, and known drug delivery devices for inhalation, suffer from numerous disadvantages. Disadvantages of MDI's have been referred to above. So far as dry powder inhalers are concerned, the gelatine capsules are not impervious to moisture. Exposure to the atmosphere can therefore result in absorption of moisture, which in turn may lead to agglomeration of the medicament powder particles. These problems may be particularly acute where as is often the case, the medicament is hygroscopic. As a result, capsules must be packaged in secondary packaging such as a blister package.

Another disadvantage is that the gelatine may be brittle, with the result that the piercing operation may produce shards or fragments which may be inhaled by the patient. This is clearly undesirable. Also, gelatine is a material of biological origin and therefore always contains a certain amount of microbiological organisms, which again is undesirable from the point of view of possible contamination of the medicament.

Removal of the capsule from the secondary packaging and loading it into the device may require a degree of dexterity greater than that possessed by some patients. In addition, the motion of the elongate gelatine capsule within the device may be irregular, leading to incomplete or variable dispensing of the powdered medicament.

Novel drug delivery devices for the administration of medicament by inhalation, and novel forms of packaging for such medicaments, have now been devised, which overcome or substantially mitigate the above-mentioned problems.

SUMMARY OF THE INVENTION

According to a first aspect of the invention there is provided a system for the administration of a powdered medicament by inhalation, the system comprising a container containing a unit dose of medicament in powder form, the container having at least one dispensing aperture, and a device having a chamber adapted to receive said container, the device further comprising air inlet means by which air may be drawn into the chamber and mouthpiece means by which air and entrained medicament may be drawn out of the chamber, wherein the chamber is substantially circular or annular in form and, in use, the container follows an orbital path within the chamber.

The system according to the invention is advantageous primarily in that it may provide improved performance in terms of the dispersion of the medicament dispensed from it, ie the proportion of the medicament which is in the form of particles fine enough to penetrate deep into the patient's airways. Loading of the medicament container into the device is easy to perform. Emptying of the medicament container may be better than with other, known devices, leading to accurate and reproducible dosing. The airflow required to generate motion of the container within the device may be relatively low, enabling the device to be used with confidence by patients with weak lung function. In addition, the device is of compact and simple construction, leading to reduced manufacturing cost and longer lifetime. It may also be possible for a wide range of differently sized medicament containers to be utilised in association with the same device.

The air inlet means are preferably arranged such that air enters the chamber substantially tangentially so as to as to facilitate the orbital motion of the container within the chamber. There are preferably provided a plurality of air inlets, most preferably opening into the chamber at substantially equiangularly spaced positions. The air inlets may include narrowed portions to act as venturi and thereby increase the speed of the airflow.

It is particularly preferred that a part of the wall of the chamber into which the air inlets open should be continuous and unbroken. This inhibits any tendency for the movement of the container to be affected by the edges of the air inlet openings. In preferred embodiments, the air inlets open into the peripheral (commonly circular) wall of the chamber, but have a depth which is less than the height of that wall so that at least part of the wall, eg the lower and/or upper part of the wall, forms an uninterrupted annular surface.

The chamber may be provided with a formation which serves to constrain the movement of the container in its orbital path. For example, a spigot or the like may be formed in the centre of the chamber. However, in practice it is commonly found that no such formation is necessary, or merely a vestigial formation, eg a small protrusion in the centre of the base of the chamber, is effective.

According to another aspect of the invention, there is provided a device having a chamber adapted to receive a container containing a unit dose of medicament in powder form, air inlet means by which air may be drawn into the chamber and mouthpiece means by which air and entrained medicament may be drawn out of the chamber., wherein the chamber is substantially circular or annular in form and is provided with one or more formations effective to constrain, in use, the container to an orbital path within the chamber.

Air preferably passes out of the chamber to the mouthpiece through a mesh or grid formed in part of the wall of the chamber. Most preferably. the mesh or grid lies in a plane which is parallel to the plane in which container moves. For example the mesh or grid may be formed in the flat base or roof of the chamber. The mesh or grid may take any suitable form provided that, in use, it serves to retain the container within the chamber whilst permitting air and entrained medicament to pass out of the chamber.

It is particularly preferred that the grid or mesh should extend over only part of the base of the chamber, most preferably the central part of the base, ie the radially outer part of the base is preferably solid. It is found that this arrangement increases the residence time of medicament dispensed from the device within the chamber and this in turn enhances the dispersion of the medicament particles. Most preferably, for a chamber with a circular of substantially circular base, the outermost part of the base forms an annulus having a width corresponding to at least 15% of the radius of the base, more preferably at least 20%.

The mouthpiece is preferably formed at the open end of a passageway or conduit which connects the chamber to the mouthpiece. A particularly compact arrangement is provided if the passageway or conduit is disposed substantially orthogonally to the axis of rotation of the container in the chamber. In other embodiments, the passageway or conduit may be oriented parallel to that axis.

The device may be manufactured from materials conventionally utilised in inhalation drug delivery devices. Examples include plastics materials such as polycarbonate, polyolefins such as polypropylene or polyethylene, and others. Other materials which may be used include metals eg aluminium stainless steel etc. Combinations of materials may be used, individual components being formed from the most suitable material in each case.

The device according to the invention may be configured for repeated use, in which case means are provided for introducing a container into the chamber and removing the container after use. The chamber may, for example, have a removable cover, eg having a snap fit or hinged connection to the rest of the device, which can be opened to insert a container, closed during use of the device and then opened again for removal of the spent container.

In other embodiments, the device may be for single dose use. In such a case the device may be supplied with a container of medicament incorporated into the device in such a way that the dispensing aperture is sealed, the container being released from the device, and the dispensing aperture thereby opened, by the patient immediately before use.

The medicament container according to the invention may have any shape, provided that shape permits the orbital motion of the container within the chamber. However, the container is preferably circular or substantially circular, ie with the overall shape of a drum, discus or short cylinder. Such a container shape is novel and represents a further aspect of the present invention, which thus provides a unit dose of a powdered inhalation medicament contained within a cylindrical or substantially cylindrical container. The diameter of the cylinder is generally greater than its depth, most preferably about twice the depth or more.

The medicament container is most preferably cylindrical or substantially cylindrical. Most preferably, the container is formed from two cooperating components which fit together, eg with a close or snap fit. One of said components is preferably of generally cylindrical construction, and open at one end. The other component will fit closely within or about the open end of the first, thereby completing the cylindrical container. One or both of the two components may be formed with a dispensing aperture. Alternatively, the at least one dispensing aperture may be defined between the two components. Most preferably, a plurality of dispensing apertures are provided, preferably four or more, eg six or eight. The apertures may advantageously be disposed around the circumference of the cylindrical container. In other embodiments, a dispensing aperture may alternatively or in addition be provided in one or both end faces of the cylinder.

The medicament container is preferably of a material which is substantially impermeable to moisture. This is advantageous in that the need for secondary packaging is thereby reduced or eliminated. This reduces the complexity of the manufacturing operation and also simplifies use of the medicament.

Thus, according to another aspect of the present invention, there is provided a unit dose of a powdered inhalation medicament, said unit dose being contained within a container having at least one dispensing aperture, the container being of a material which is substantially impermeable to moisture.

Because the container is provided with at least one dispensing aperture it is not necessary for it to be pierced prior to use and there are therefore no problems such as those associated with the piercing of conventional gelatine capsules.

In order to prevent loss of powder from the container, the unit dose according to the invention will, prior to use, be associated with a sealing means arranged to close the at least one dispensing aperture. Thus, according to a further aspect of the invention, a medicament package containing at least one unit dose of a powdered medicament comprises a container which contains the unit dose of medicament and has at least one dispensing aperture, the container being of a material which is substantially impermeable to moisture, and a sealing means arranged to close the at least one dispensing aperture.

The medicament container may be formed from any material or combination of materials with the requisite impermeability to moisture. One preferred example is light metal sheet, eg aluminium, from which the components making up the container may be pressed and cut. Other metals include stainless steel and alloys. Other materials which may be used include plastics materials. Examples of plastics materials of low moisture permeability are high density polyethylene (eg that sold under the trade mark RIGIDEX HD6070EA), polycarbonate, polyvinylchloride, polyethylene terephthalate and polypropylene. One particular plastics material which may be suitable is the olefin-cycloolefin copolymer sold by Hoechst AG under the trade mark TOPAS.

By "low moisture permeability" is meant a permeability to water vapour which is sufficiently low that during normal storage and use of the container (and in the absence of secondary packaging such as a blister package) ingress of moisture is insufficient to affect the medicament adversely to a significant extent. Permeability may be measured by standard methods such as ASTM F1249/90. When measured by that method at a temperature of 38° C. and 90% relative humidity the permeability of the material is preferably less than 0.5 g mm/m$^2$ day bar, more preferably less than 0.3, and especially less than 0.1.

In general, the lower the moisture permeability of the material used for the container, the lower is the thickness of that material required to form an effective barrier to moisture. This leads to a reduction in weight and hence to a reduction in the airflow necessary to cause the container to move.

The sealing means may comprise a ring of elastomeric material which surrounds the container so as to overlie and close the at least one dispensing aperture.

Alternatively, the sealing means may be a support which carries the medicament container. For example, the sealing means may be a planar support having an opening or recess within which the container is received with a close fit such that the support overlies and closes the at least one dispensing aperture. The support may, for example, be of card or plastics material. In one embodiment, the support comprises a sheet of plastics material, the sheet having an opening dimensioned and configured closely to receive the container, and the circumference of said opening being constituted by a ring of elastomeric material. Suitable elastomeric materials include natural and synthetic rubbers, and so-called thermoplastic elastomers, eg that known as SANTOPRENE. The elastomeric material may be chemically or physically bonded or fixed to the support.

The system according to the invention may be used for the delivery of a wide range of medicaments, including any medicament which is suitable for delivery in powder form by inhalation. Inhalation will most commonly be oral inhalation, but may also be nasal inhalation, in which case the term "mouthpiece" will be understood to refer to a passage suitable for insertion into a nostril rather than the patient's mouth.

Whilst the system of the invention is intended primarily for use in which inspiration by the patient leads to the necessary motion of the container and dispersion of the medicament from the container, an external source of air or other gas may alternatively be used to create the necessary airstream.

According to another aspect of the invention, there is provided a method for the administration of a powdered medicament by inhalation, which method comprises introducing into a chamber which is substantially circular or annular in form a container containing a unit dose of the medicament, the container having at least one dispensing aperture therein, and generating an airstream within the chamber so as to cause the container to follow an orbital path within the chamber.

The movement of the container within the chamber is preferably epicyclic, ie the container orbits about the centre of the chamber and also rotates about its own axis.

BRIEF DESCRIPTION OF THE DRAWINGS

Currently preferred embodiments of the invention will now be described in greater detail, by way of illustration only, with reference to the accompanying drawings, in which.

DETAILED DESCRIPTION OF THE INVENTION

Referring first to FIGS. 1 to 4, a first embodiment of an inhaler according to the invention is generally designated 10. The inhaler 10 comprises a lower part 11 and an upper part 12 which are both moulded in plastics material and hingedly connected together. The lower part 11 and upper part 12 can be opened, as shown by the broken lines in FIG. 2, and pressed together to the position shown by the solid lines in FIG. 2. The upper surface of the lower part 11 has a pair of upstanding latch formations 13 which engage in corresponding recesses (not visible) in the underside of the upper part 12 to hold the two parts 11,12 in engagement.

Figure 1:
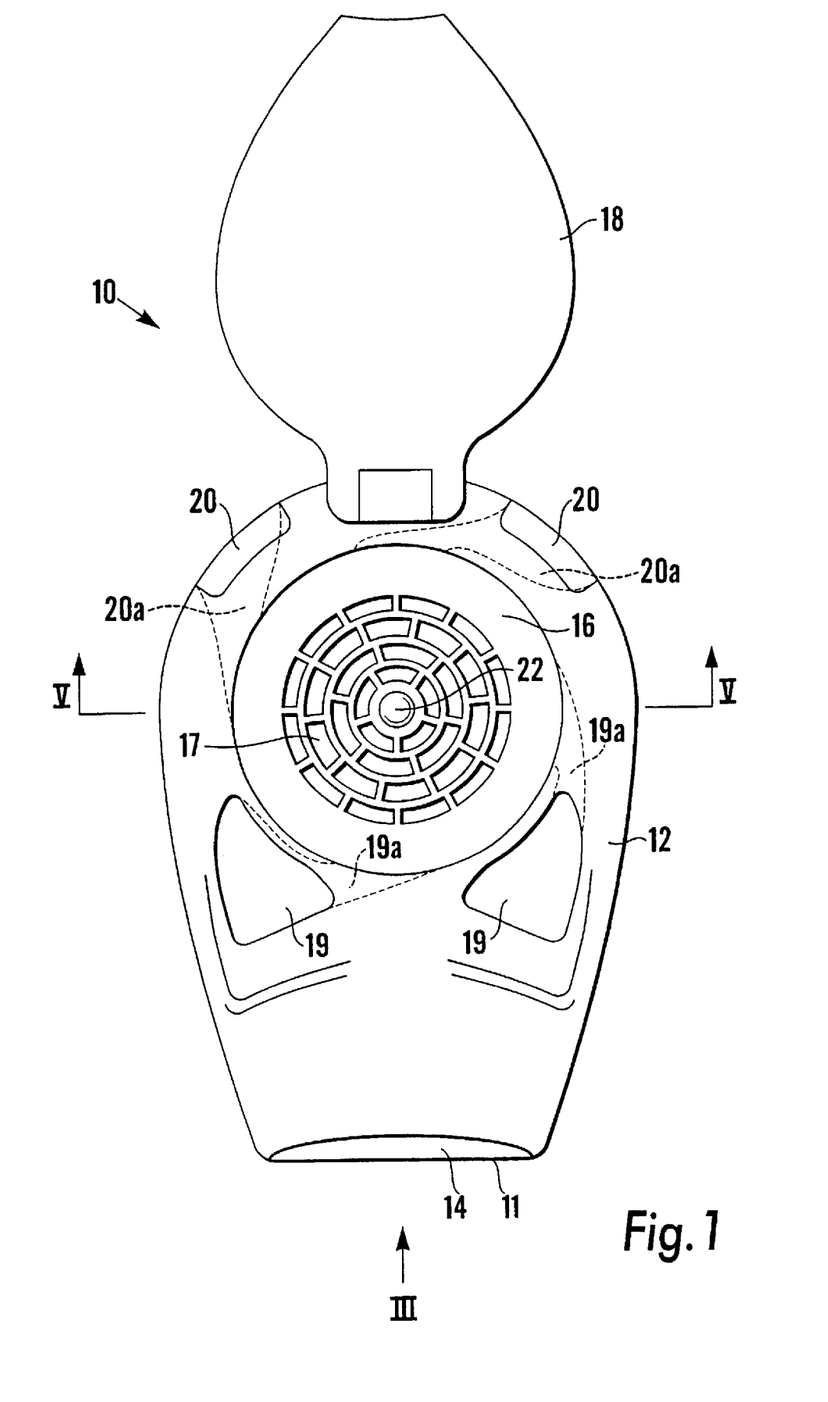
FIG. 1 is a plan view of a first, presently preferred embodiment of a powdered medicament inhaler according to the invention, in an open, unloaded condition.

Corresponding recesses extend longitudinally in the upper surface of the lower part 11 and the lower surface of the upper part 12 and together define a passageway 14 which extends from the front of the inhaler 10 towards the hinged connection. The open end of this passageway 14 serves as a mouthpiece.

A circular chamber 16 is formed in the upper part 12. The chamber 16 communicates with the passageway 14 by means of a series of openings which make up a generally circular grid 17 in the centre of the base of the chamber 16. The central part of the base of the chamber 16, which is surrounded by the grid 17, is solid and is formed with a generally hemispherical bulge 22.

Figure 2:
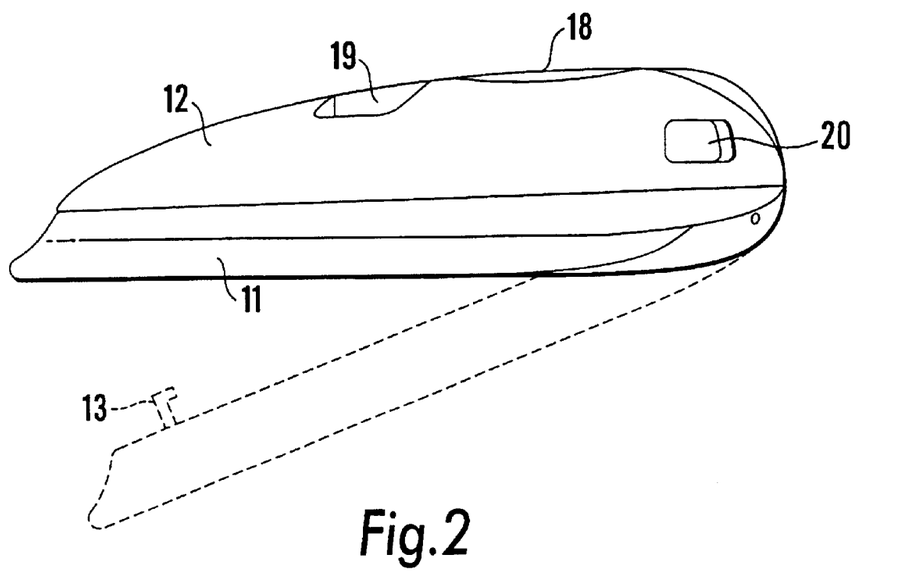
FIG. 2 is a side elevational view of the inhaler of FIG. 1.
Figure 3:
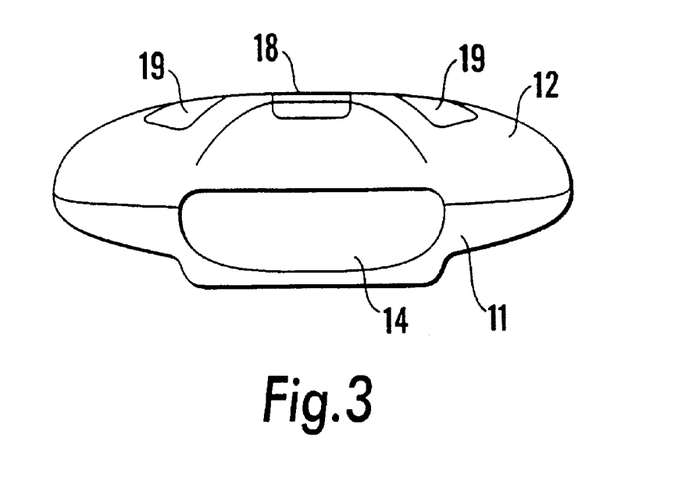
FIG. 3 is a front elevational view of the inhaler of FIG. 1, on the arrow III in FIG. 1.
Figure 4:
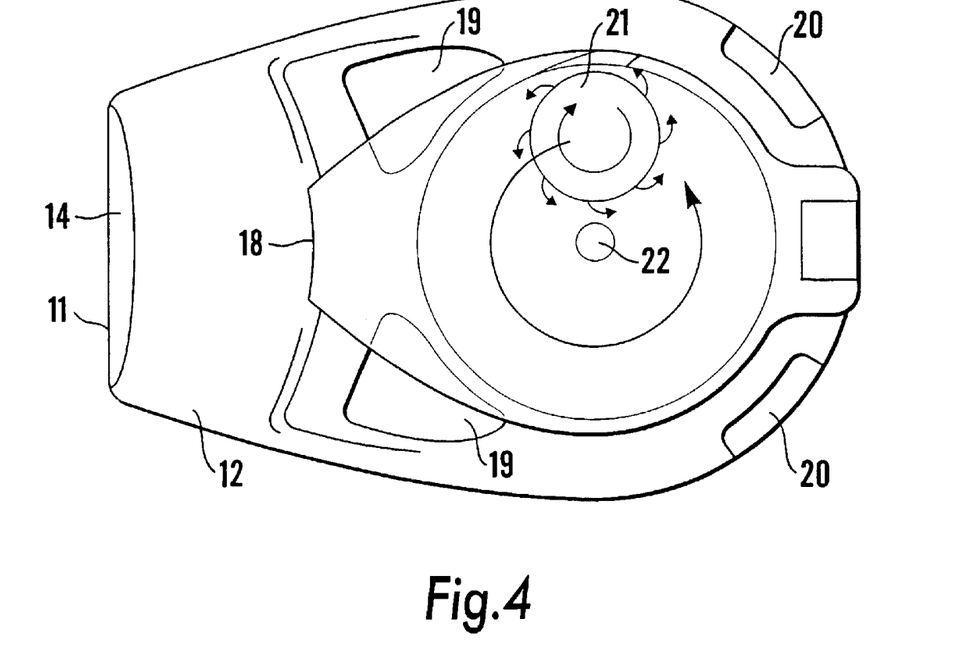
FIG. 4 is a plan view of the inhaler of FIG. 1 in a closed loaded condition, indicating also the movement of a medicament container within the inhaler.

A clear plastics lid 18 is hingedly connected to the upper part 12 and is moveable from an open position, as shown in FIG. 1 to a closed position shown in FIGS. 2 and 4.

Also formed in the upper part 12 are two front air inlets 19 and two rear air inlets 20 which connect the exterior of the inhaler 10 with the wall of the chamber 16 by means of respective conduits 19*a*,20*a* which are shown by broken lines in FIG. 1. The conduits 19*a*,20*a* are aligned substantially tangentially to the wall of the chamber 16 and connect to the chamber 16 at substantially equiangularly spaced locations.

The inhaler 10 is used to deliver medicament from a medicament container such as is described in more detail below. Typically, such a container comprises a circular drum of aluminium or other substantially moisture impervious material with a series of openings disposed around its circumference. In use, the lid 18 is moved to the open condition and such a container 21 (see FIG. 4) is introduced into the chamber 16. The lid 18 is then closed. The patient then places the open end of the passageway 14 to his mouth and inhales. Air is drawn through the air inlets 19,20, along the conduits 19*a*,20*a* and substantially tangentially into the chamber 16. The airstream passes through the grid 17 and along the passageway 14 to the patient's mouth.

The stream of air entering the chamber 16 tangentially causes the container 21 to orbit about the centre of the chamber 16, movement of the container 21 being constrained by the side wall of the chamber 16 and medicament being dispensed from within the container 21 through the openings in the container 21. The medicament is entrained in the airstream which passes out of the chamber 16 through the grid 17 and is inhaled by the patient.

It is commonly observed that, as shown in FIG. 4. the motion undergone by the container 21 is epicyclic, ie the container orbits around the centre of the chamber 16, being constrained by the wall of the chamber 16, whilst simultaneously spinning about its own axis. The bulge 22 in the centre of the chamber 16 also assists in maintaining the orbital path of the container 21. For clarity, the grid 17 is omitted from FIG. 4.

As is also shown by short arrows in FIG. 4, medicament powder is dispensed from the container 21, under the influence of centrifugal forces, in substantially all directions, ie towards the centre of the chamber as well as towards its perimeter. This is in contrast to dispersal of medicament from the ends of a rotating gelatine capsule. in such a case, the medicament is ejected only towards the side wall of the chamber.

The movement of the container 21 as it spins and orbits may further improve dispersion of the medicament by creating a milling effect between the container 21 and the side wall of the chamber 16. This action may also inhibit deposition of medicament within the chamber 16, ie there may be a "self-cleaning" effect.

Figure 5:
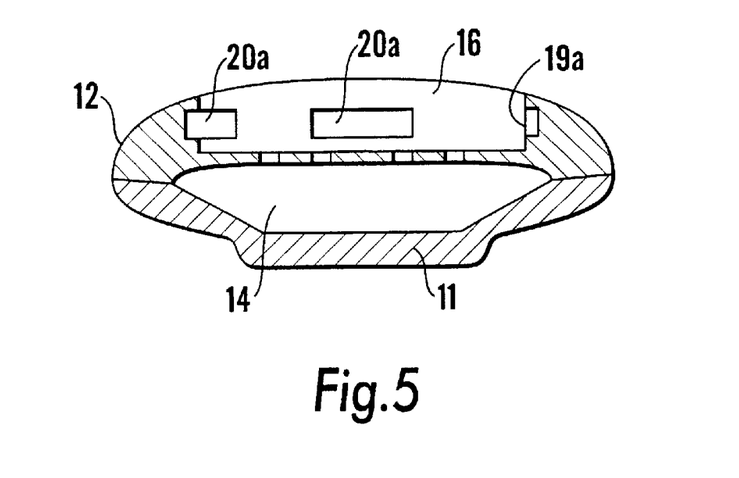
FIG. 5 is a sectional view on the line V—V in FIG. 1
Figure 6:
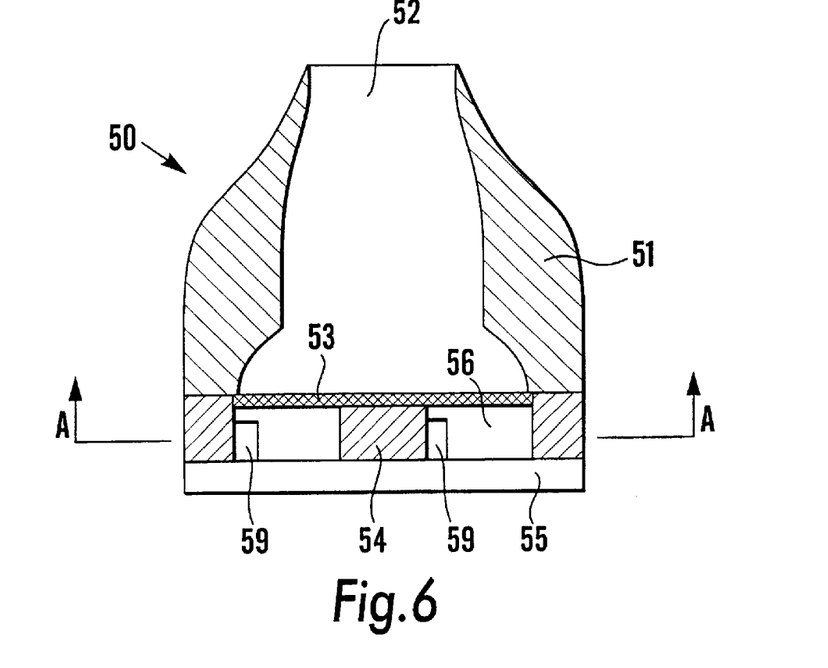
FIG. 6 is a view in longitudinal section of a second embodiment of a powdered medicament inhaler according to the invention.

As can be seen from FIG. 5, the conduits 19*a*,20*a* open into the wall of the chamber 16 at positions slightly spaced from the base of the chamber 16. The lower part of the wall of the chamber 16 is thus continuous and unbroken. This is beneficial since it inhibits any tendency of the edges of the conduits 19*a*,20*a* to foul the movement of the container 21 within the chamber 16, thereby improving the uniformity and smoothness of that movement and enhancing the dispersion of medicament from the container 21.

The fact that the grid 17 is formed only in the central portion of the base of the chamber 16 is also found to be beneficial. It is believed that this increases the residence time in the chamber 16 of medicament particles dispensed from the container 21, leading to improved dispersion of the medicament in the airstream inhaled by the patient.

Figure 8:
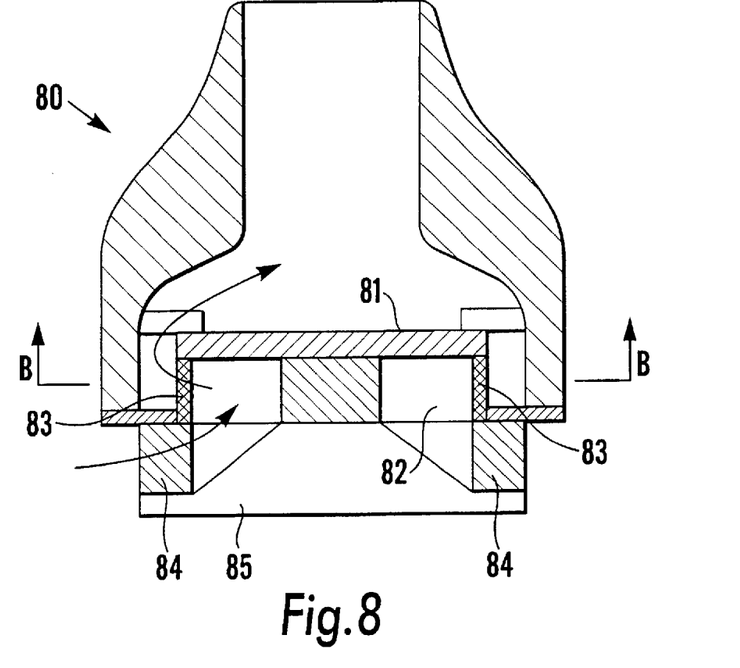
FIG. 8 is a view in longitudinal section of a third embodiment of a powdered medicament inhaler according to the invention.
Figure 9:
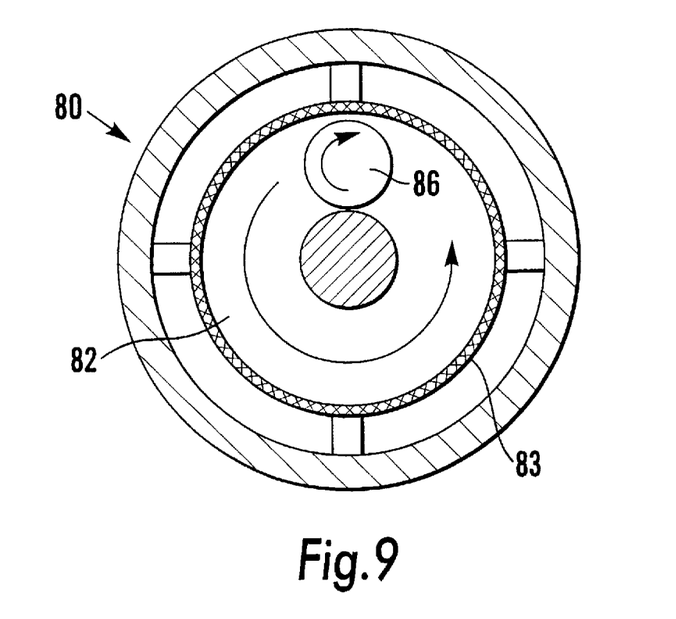
FIG. 9 is a sectional view on the line B—B in FIG. 8.

The compact, substantially flat shape of the inhaler 10 is a consequence of the fact that the passageway 14 is oriented not co-axially with, or parallel to, the axis of movement of the container 21 within the chamber 16, but instead substantially orthogonally thereto.

Turning now to FIGS. 6 and 7, a second embodiment of a powdered medicament inhaler (generally designated 50) according to the invention comprises a moulded plastics body 51 with a generally central passageway 52. The top (as viewed in FIG. 6) end of the body 51 is shaped to form a mouthpiece.

The passageway 52 is partitioned by a moulded plastics grid 53 from which depends a circular, central spigot 54. A clear plastics closure 55 is hingedly connected to the body 51. The space between the grid 53, the walls of the body 51, the closure 55 and the central spigot 54 constitutes an annular chamber 56. The closure 55 can be moved between a closed position (as shown in FIG. 6) and an open position in which a medicament container 58 may be introduced into the chamber 56.

As can be seen from FIG. 7, four equiangularly spaced tangential inlets 59 are provided in the side wall of the chamber 56. The inlets 59 include narrowed portions 60. As can be seen from FIG. 6, the inlets 59 do not extend vertically (as viewed in FIG. 6) as far as the grid 54. Rather, that part of the side wall of the chamber 56 which is immediately below the grid 54 is uninterrupted.

In use, the closure 55 is moved to the open position and a container 58 introduced into the chamber 56. The closure 55 is then closed. The container 58 contains one or more dispensing openings which are exposed in use. Medicament is thus able to escape from the container 58 via these openings.

Having loaded the chamber 56 with a medicament container 58, the user raises the device 50 to his mouth and inhales through the mouthpiece. Air is drawn into the chamber 56 through the inlets 59, the narrowed portions 60 acting as venturi and increasing the flow rate of the air. The influx of air causes the container 58 to orbit the central spigot 54 in a planetary motion and simultaneously to rotate about its own axis, as indicated by the curved arrows in FIG. 7. Medicament contained within the container 58 is acted upon by substantial centrifugal forces and thereby ejected from the container 58. The motion of the container 58 results in effectively complete emptying of the container 58. The uninterrupted portion of the side wall of the chamber 56 facilitates the planetary motion of the container 58, and prevents impact of the container 58 with the edges of the inlets 59 which might otherwise introduce irregularities into the motion of the container 58.

Because the container 58 may be light in weight (compared for example with conventional gelatine capsules) only a relatively weak airflow is required to generate motion of sufficient vigour to dispense the container contents. This a particularly significant advantage in the case of the administration of medicaments for the treatment of reversible obstructive airways disease (eg asthma), the recipients of which may have inherently weak lung function.

Dispersion of the medicament as it is dispensed from the container 58 may be further facilitated by a milling action of the rotating container 58 against the wall of the chamber 56, ie grinding of medicament between the rotating container 58 and the wall.

The embodiment (generally designated 80) shown in FIGS. 8 and 9 is similar in overall design to that of FIGS. 6 and 7, with the exception that the upper (as viewed in FIG.

8) wall 81 of the chamber 82 is solid, air (and entrained medicament) passing out of the chamber 82 via a grid 83 formed as the side wall of the chamber 82. Air inlets 84 are formed in the closure 85. In use, movement of a container 86 within the chamber 82 is similar to that described in relation to the previous embodiments, as again shown by the curved arrows.

Figure 7:
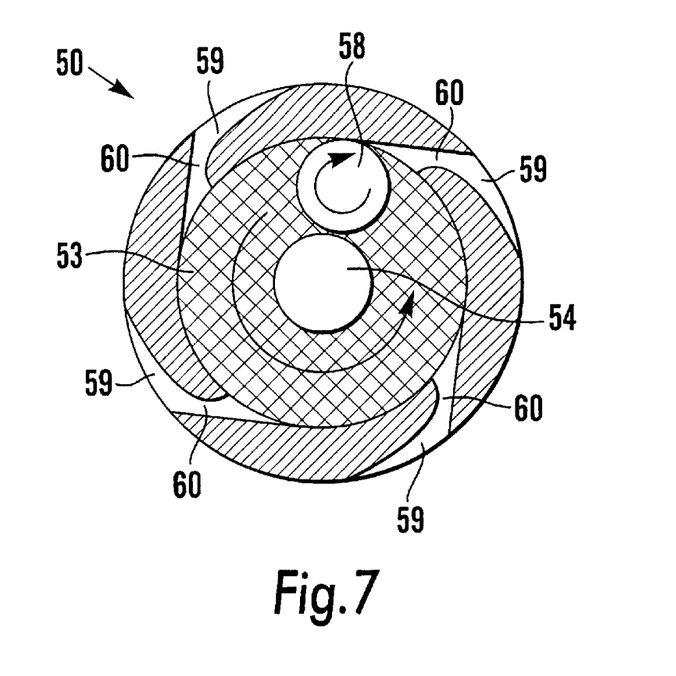
FIG. 7 is a sectional view on the line A—A in FIG. 6.
Figure 10:
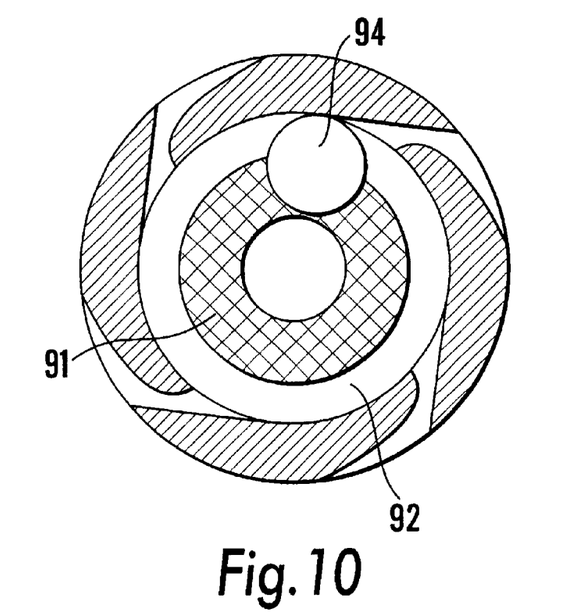
FIG. 10 is a view similar to FIG. 7 of a modified form of the inhaler of FIGS. 6 and 7.

FIG. 10 is a view similar to FIG. 7 of an embodiment in which the grid 91 does not extend over the full upper wall of the chamber. Instead, the peripheral region 92 of that upper wall is solid. As described above, it has been found that this may improve dispersion of medicament dispensed from a container 94.

Figure 11:
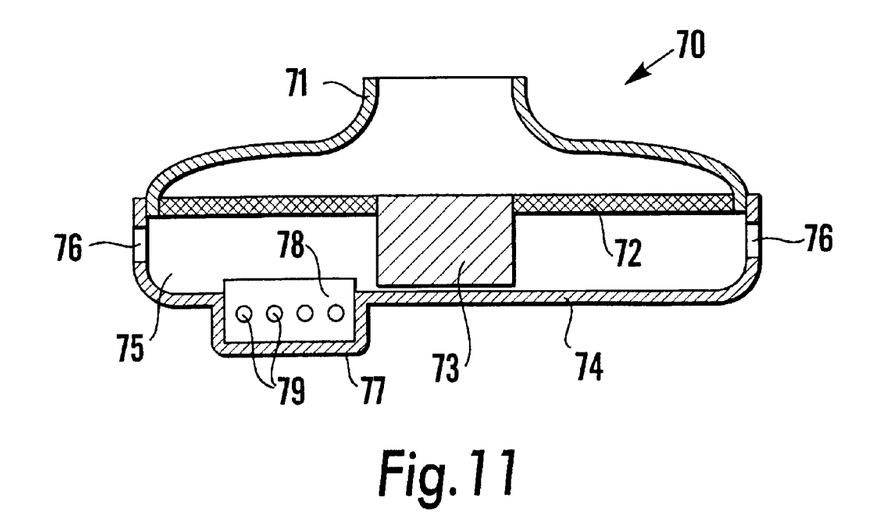
FIG. 11 is a side view in section of a fourth embodiment of a powdered medicament inhaler according to the invention.

The embodiment (generally designated 70) of FIG. 11 is a single-dose disposable unit. Again, a moulded plastics mouthpiece 71 carries a grid 72 with a central spigot 73. A flexible plastics cap 74 is fitted over the lower end of the mouthpiece 71 and forms, with the grid 72, an annular chamber 75. Air inlets 76 are formed in the cap 74 and also a container well 77 into which a container 78 is loaded prior to assembly of the unit 70. The container 78 is closely received within the well 77, the well 77 sealing dispensing openings 79 in the container 78.

In use, the container 78 is pressed out of the well 77 into the chamber 75. The patient then inhales at the mouthpiece 71, medicament being dispensed from the container 78, entrained and inhaled substantially as previously described.

One novel application of such a single-use, disposable inhaler may be for the administration of pain-killers (eg morphine) in disaster or battlefield situations.

In all the embodiments described above, various modifications may be made without departing from the essence of the invention. For instance. the central spigot described for certain embodiments may be omitted as it may not be essential for maintaining orbital motion of the container. Similarly, a central spigot may be incorporated into those embodiments in which it is not present as described above. Alternatively, the spigot may be replaced by a small raised formation, eg of generally hemispherical shape in the base of the chamber.

Figure 12:
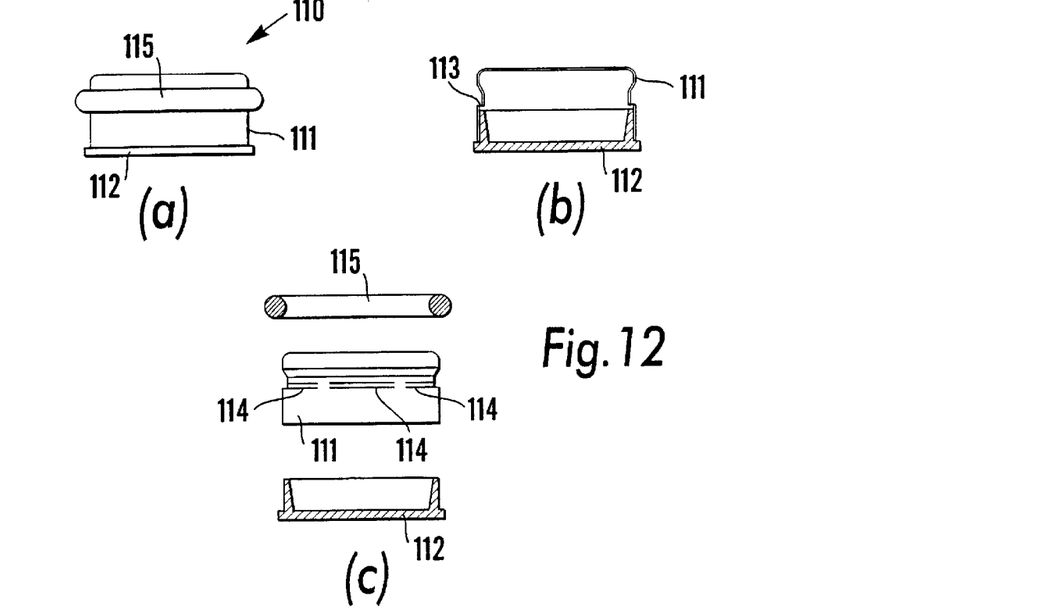
FIG. 12 shows a first embodiment of a medicament package according to the invention, in (a) side view, (b) cross-section and (c) exploded view.

Referring now to FIG. 12, a first embodiment of a medicament container according to the invention is generally designated 110 and comprises a generally cylindrical cup 111 which is pressed from thin aluminium sheet and is open at its lower (as viewed in FIG. 12) end, and a plastics bung 112 which has an upstanding rim received closely within the open lower end of the cup 111.

A circumferential groove 113 is formed in the curved surface of the cup 111, a series of elongate perforations 114 being formed at intervals in the groove 113. The assembly is completed by an O-ring 115 of elastomeric material which fits closely about the cup 111 in the region of the groove 113, and thereby seals the perforations 114. The 0-ring 115 is removed from the cup 111 immediately prior to introduction of the container 10 into a drug delivery device (for example a device of the type described above).

Figure 13:
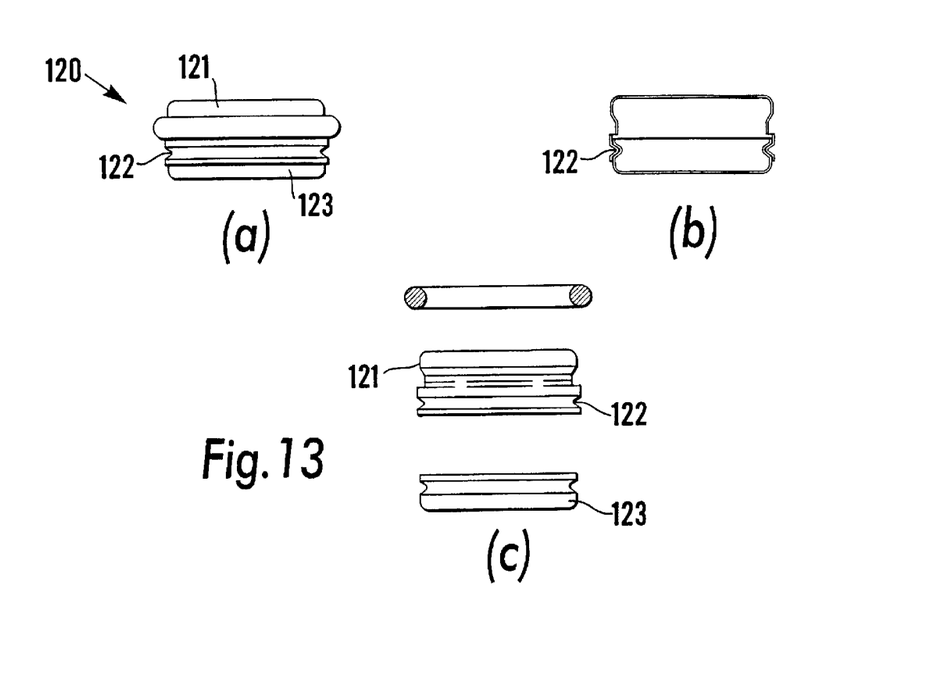
FIG. 13 shows a second embodiment of a medicament package according to the invention, in (a) side view, (b) cross-section and (c) exploded view.

The embodiment of FIG. 13 is generally designated 120 and is similar to that of FIG. 12, save that the lower part of the cup 121 is formed with a second groove 122 which has a snap fit with a correspondingly shaped upper part of a second cup 123. The second cup 123 fits closely within the lower part of the cup 121, and performs the same function as the bung 112 of the first embodiment 110.

Figure 14:
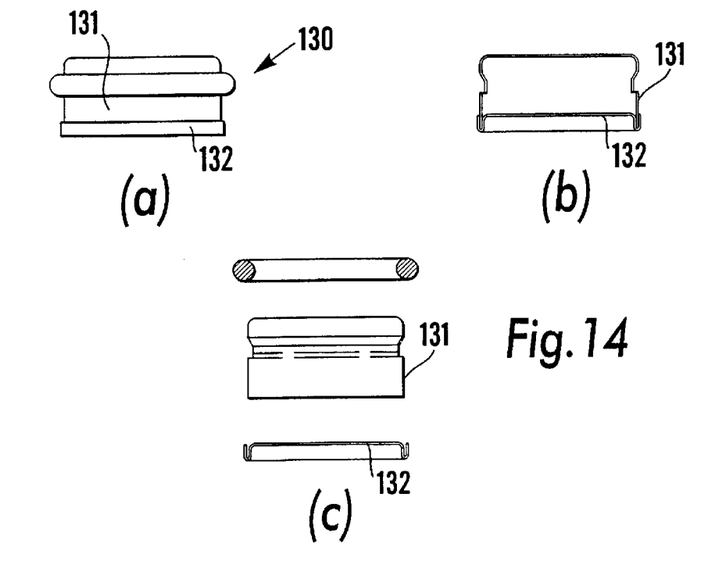
FIG. 14 shows a third embodiment of a medicament package according to the invention, in (a) side view, (b) cross-section and (c) exploded view.

In the embodiment 130 of FIG. 14, the lower end of the cup 131 is received in a circumferential groove in a base plate 132, the two components being crimped to form a tight seal.

Figure 15:
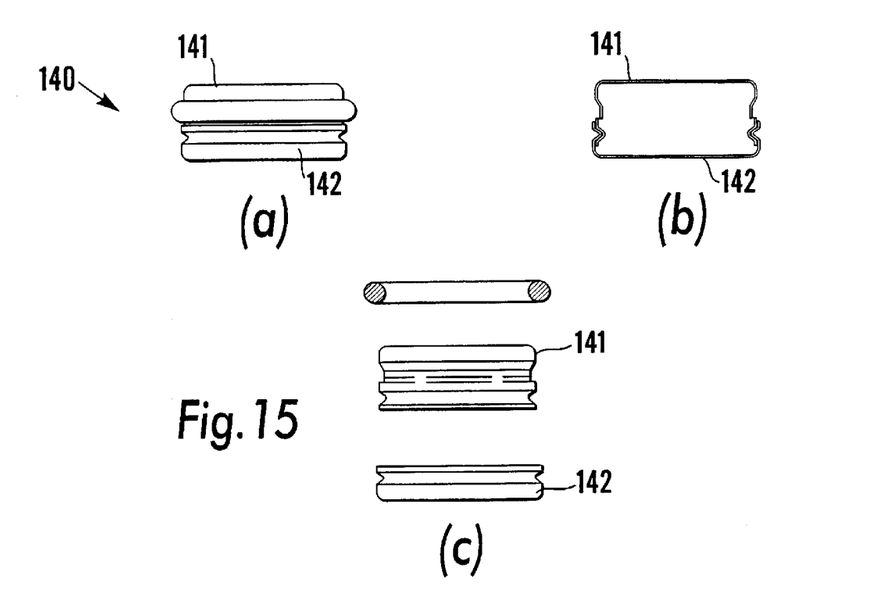
FIG. 15 shows a fourth embodiment of a medicament package according to the invention, in (a) side view, (b) cross-section and (c) exploded view.

The container 140 of FIG. 15 is similar to that 120 of FIG. 13, except that the lower cup 142 fits externally about the lower, open end of the main cup 141.

Figure 16:
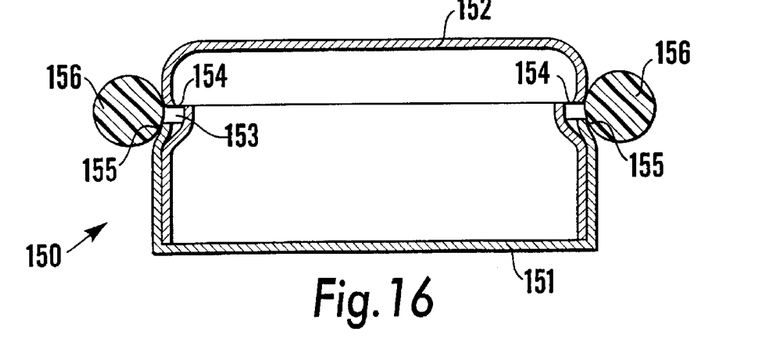
FIG. 16 is a sectional view of a fifth embodiment of a medicament package according to the invention.

FIG. 16 shows a cross-sectional view of yet a further embodiment 150 of a medicament container according to the invention, which again comprises a pair of interfitting cup components (a base cup 151 and an upper cup 152) pressed from lightweight aluminium sheet. In this case, the upper cup 152 is formed with a circumferential groove 153 which is perforated at intervals to define openings 154. The open end of the upper cup 152 is received closely within the base cup 151 which extends upwardly as far as the groove 153, the upper rim of the base cup 151 being deformed inwardly to form a lip 155 which cooperates with the groove 153 so as to retain the base cup 151 and upper cup 152 in engagement. An 0-ring 156 which fits, as for the other embodiments described above, closely around the groove 153 thus serves to seal not only the openings 154, but also the joint between the base cup 151 and the upper cup 152.

Figure 17:
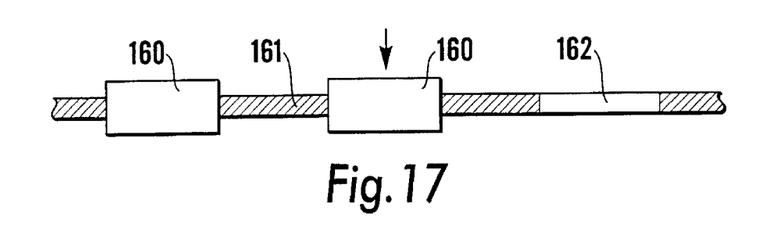
FIG. 17 shows a plurality of medicament containers according to the invention mounted in a first form of support.

Turning now to FIG. 17, this shows another form of package according to the invention. Containers 160 are represented schematically as rectangles in FIG. 16 but may be similar to any of those described above. In this case, the containers 160 are sealed not by a sealing ring, but by a plastics sheet 161 with circular apertures 162 into which the containers 160 are pressed with a close, interference fit. The thickness of the sheet 161 is sufficient for it to cover (and hence seal) openings in each container 160. The sheet 161 also serves as a support for the containers 160 and may carry printed matter relating to the medicament (eg instructions for use, dosage information etc). Instead of plastics material, the sheet 161 may be formed of any other suitable material, eg cardboard (which may in turn be coated with a plastics material). A container 160 may be removed from the package simply by manual pressure on one of the exposed faces of the container 160 (as indicated by the arrow in FIG. 17), eg dislodging the container 160 directly into a dispensing device.

Figure 18:
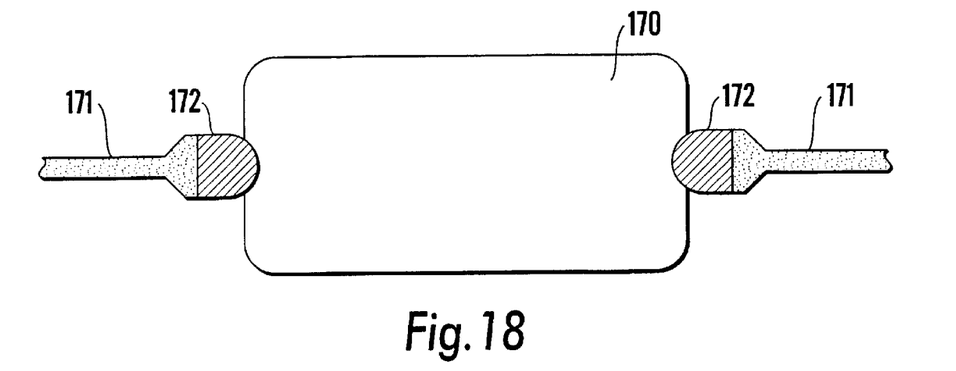
FIG. 18 shows a sectional view of a medicament container according to the invention mounted in a second form of support.

FIG. 18 shows a detailed view of part of a modified package broadly similar to that just described. This comprises a medicament container 170, again represented schematically in FIG. 18 but which may be similar to any of those described above, which is received in a circular opening in a sheet 171 of plastics material. This embodiment exhibits the additional feature that the periphery of the circular opening is formed by a ring 172 of elastomeric material which is bonded to the rest of the sheet 171.

Figure 19:
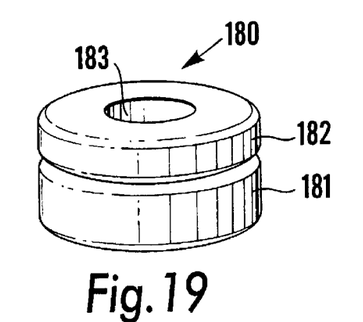
FIG. 19 shows a perspective view of a sixth embodiment of a medicament container according to the invention.
Figure 20:
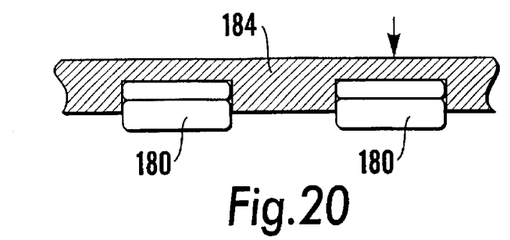
FIG. 20 is a sectional view of medicament containers of the form shown in FIG. 19 mounted in a third form of support.

FIG. 19 shows a further form of circular container 180, again formed from two interfitting cups 181,182. In this embodiment, however, there are no dispensing openings around the periphery. Instead, the top face of the upper cup 182 has a central opening 183. FIG. 20 shows a partial sectional view of a package including such containers 180. The package comprises a sheet 184 of resilient plastics or elastomeric material having circular recesses into which the containers 180 are pressed. The sheet 184 thus surrounds and seals the open faces of the containers 180. Again, a container 180 may be dislodged from the package simply by the application of manual pressure to the sheet 184 (again indicated by an arrow in FIG. 20).

It will be appreciated that the containers described above may, instead of aluminium, be formed from other, suitably moisture impervious materials such as plastics materials.

Figure 21:
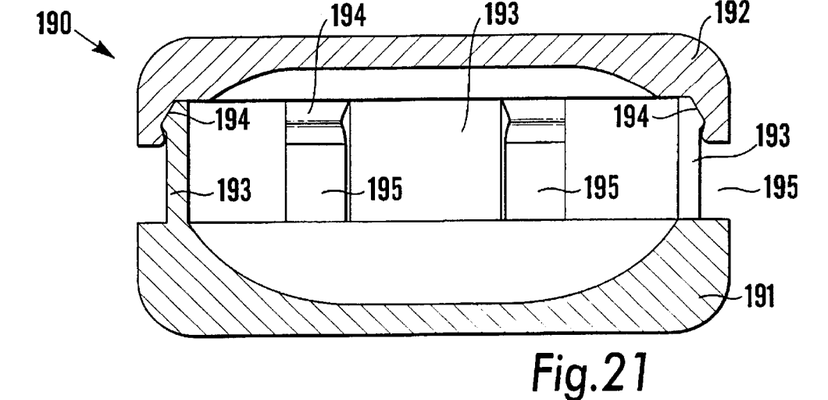
FIG. 21 is a sectional view of a seventh embodiment of a medicament container according to the invention.

FIG. 21 is a cross-sectional view of one such container 190 of plastics material. The container 190 comprises a base cup 191 and an upper cup 192. The two components 191,192 have a snap fit by virtue of an upstanding clip formation 193 formed on the base cup 191 which engages in a corresponding recess 194 in the upper cup 192. The clip formation 193 is interrupted by openings which in the assembled container 190 constitute dispensing apertures 195. A plurality of such apertures 195 are provided, around the periphery of the container 190, the sectional view in FIG. 21 being drawn through one such aperture 195.

The cups 191, 192 are formed by moulding with curved internal surfaces which aid dispensing of medicament through the apertures 195. In addition, the greater thickness of plastics (and hence the greater mass) in the radially outward part of the container 190 encourages a flywheel effect which assists spinning of the container 190.

Figure 22:
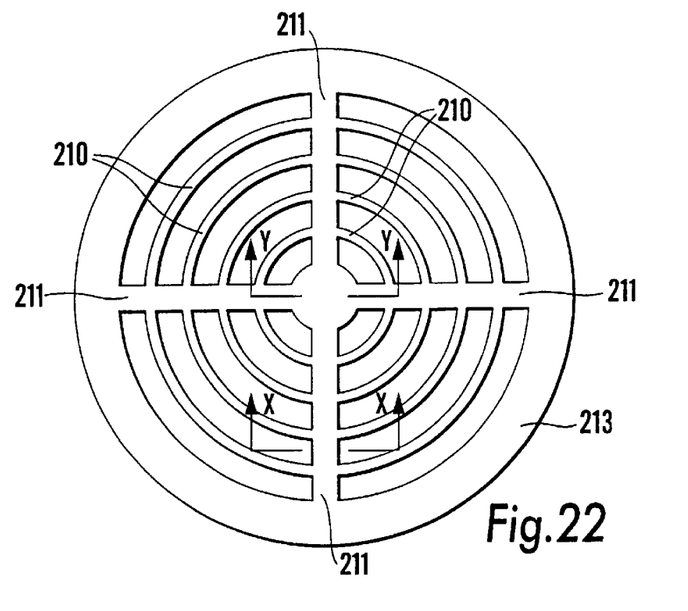
FIG. 22 is a plan view of an alternative form of grid which may be incorporated into several of the embodiments shown in the foregoing Figures.
Figure 23:
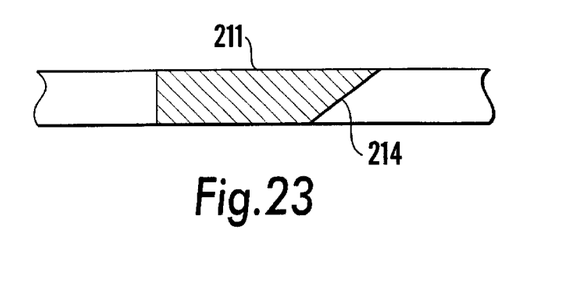
FIG. 23 is a scrap section on the line X—X in FIG. 21.
Figure 24:
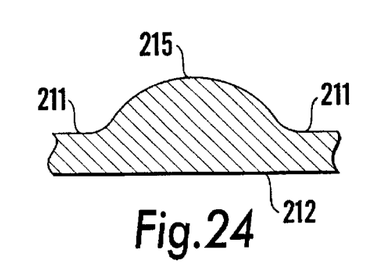
FIG. 24 is a scrap sectional view on the line Y—Y in FIG. 21.

Referring now to FIGS. 22 to 24, an alternative form of grid for incorporation into a device such as described above comprises concentric rings 210 supported by a pair of cross-bars 211 which extend in cruciform fashion diametrically across the grid between a circular central portion 212 and a peripheral annulus 213.

As shown in FIG. 23, the edge 214 of each cross-bar 211 which is upstream in relation to the airflow through the grid is inclined to facilitate airflow across it (as shown by the arrow in FIG. 23). This feature has the important advantage of reducing impaction and build-up of medicament on the cross-bars 211.

FIG. 24 shows that the central portion 214 has a raised part 215 which serves to constrain a medicament container to an orbital path. Such a formation may not be necessary and in other embodiments, as in some of those described above, may be omitted.

What is claimed is:

1. A system for the administration of a powdered medicament by inhalation, the system comprising a container containing a unit dose of medicament in powder form, the container having at least one dispensing aperture and being cylindrical or substantially cylindrical in shape, the diameter of the container being greater than its depth and the container being formed from first and second cooperating components, and a device having a chamber adapted to receive said container, the device further comprising air inlet means by which air may be drawn into the chamber and a mouthpiece by which air and entrained medicament may be drawn out of the chamber, wherein the chamber is substantially circular or annular in form and, in use, the container follows an orbital path within the chamber.

2. A system as claimed in claim 1, wherein the air inlet means are arranged such that air enters the chamber substantially tangentially so as to facilitate orbital motion of the container within the chamber.

3. A system as claimed in claim 1, wherein a part of a wall of the chamber into which the air inlet means open is continuous and unbroken.

4. A system as claimed in claim 3, wherein the air inlet means open into a peripheral wall of the chamber, which peripheral wall has a height, but said air inlet means have a depth which is less than said height so that at least part of said peripheral wall forms an uninterrupted annular surface.

5. A system as claimed in claim 1, wherein the chamber is provided with a formation which serves to constrain the movement of the container to the orbital path.

6. A system as claimed in claim 5, wherein said formation is a protrusion in the centre of the chamber.

7. A system as claimed in claim 1, wherein air passes out of the chamber to the mouthpiece through a mesh or grid formed in part of a wall of the chamber.

8. A system as claimed in claim 7, wherein the mesh or grid is formed in a base of the chamber and a radially outer part of the base is solid.

9. A system as claimed in claim 1, wherein the mouthpiece is formed at the open end of a passageway or conduit which connects the chamber to the mouthpiece and the passageway or conduit is disposed substantially orthogonally to an axis of rotation of the container in the chamber.

10. A system as claimed in any preceding claim, wherein the device is configured for repeated use, and means are provided for introducing a container into the chamber and removing the container after use.

11. A system as claimed in claim 1, which is for single dose use and is supplied with a container of medicament incorporated into the device in such a way that the dispensing aperture is sealed, the container being released from the device, and the dispensing aperture thereby opened, by the patient immediately before use.

12. A system as claimed in claim 1, wherein said first cooperating component is of generally cylindrical construction and has an open end, said second cooperating component fitting closely within or about the open end of the first cooperating component.

13. A system as claimed in claim 1, wherein the container is provided with a plurality of dispensing apertures.

14. A system as claimed in claim 1, wherein the container is of a material which is substantially impermeable to moisture.

15. A system as claimed in claim 1, wherein the container is formed at least in part from metal sheet.

16. A system as claimed in claim 15, wherein the metal sheet is aluminium sheet.

17. A system as claimed in any preceding claim, wherein the motion of the container, in use, is epicyclic.

18. A method for the administration of a powdered medicament by inhalation, which method comprises:
   a) providing a container containing a unit dose of said powdered medicament, the container having at least one dispensing aperture and being cylindrical or substantially cylindrical in shape, the diameter of the container being greater than its depth and the container being formed from first and second cooperating components,
   b) providing a device having a chamber adapted to receive said container, the device further comprising air inlet means by which air may be drawn into the chamber and a mouthpiece by which air may be drawn out of the chamber, the chamber being substantially circular or annular in form, and
   c) generating an airstream within the chamber by drawing air from the chamber via the mouthpiece so as to cause the container to follow an orbital path within the chamber, powdered medicament thereby being dispensed from within the container via said at least one dispensing aperture, entrained in said airstream and withdrawn from the chamber.

19. A method as claimed in claim 18, wherein the motion of the container is epicyclic.

20. A device for the administration of a powdered medicament to a patient by inhalation, which device has a chamber adapted to receive a container containing a unit dose of medicament in powder form, the container having a dispensing aperture, air inlet means by which air may be drawn into the chamber and a mouthpiece by which air and entrained medicament may be drawn out of the chamber, wherein the chamber is substantially circular or annular in form and is provided with one or more formations effective to constrain, in use, the container to an orbital path within the chamber, said one or more formations comprising a spigot or the like in the centre of said chamber, and wherein the device is for single dose use and is supplied with the container of medicament incorporated into the device in such a way that the dispensing aperture is sealed, the container being released into the chamber, and the dispensing aperture thereby opened, by the patient immediately before use.

21. A device as claimed in claim 20, wherein the air inlet means are arranged such that air enters the chamber substantially tangentially so as to facilitate orbital motion of the container within the chamber.

22. A device as claimed in claim 20, wherein a part of a wall of the chamber into which the air inlet means open is continuous and unbroken.

23. A device as claimed in claim 22, wherein the air inlet means open into a peripheral wall of the chamber, but have a depth which is less than a height of said peripheral wall so that at least part of said peripheral wall forms an uninterrupted annular surface.

24. A device as claimed in claim 20, wherein said spigot or the like is a protrusion in the centre of a base of the chamber.

25. A device as claimed in claim 20, wherein air passes out of the chamber to the mouthpiece through a mesh or grid formed in part of a wall of the chamber.

26. A device as claimed in claim 25, wherein the mesh or grid is formed in a base of the chamber and a radially outer part of the base is solid.

27. A device as claimed in claim 20, wherein the mouthpiece is formed at an open end of a passageway or conduit which connects the chamber to the mouthpiece and the passageway or conduit is disposed substantially orthogonally to an axis of rotation of the container in the chamber.

28. A cylindrical or substantially cylindrical container having at least one dispensing aperture, the diameter of the container being greater than its depth, the container being of a material which is substantially impermeable to moisture, the container being formed from first and second cooperating components, wherein said first cooperating component is of generally cylindrical construction and has an open end, said second cooperating component fitting closely within or about the open end of the first cooperating component, and the container having contents consisting essentially of a single unit dose of a powdered inhalation medicament.

29. A container as claimed in claim 28, wherein the container is formed at least in part from metal sheet.

30. A container as claimed in claim 29, wherein the metal sheet is aluminium sheet.

31. A medicament package containing at least one unit dose of a non-pressurised, dry powdered inhalation medicament, said medicament package comprising a container which contains a unit dose of non-pressurised, dry powdered inhalation medicament and has at least one dispensing aperture, the container being of a material which is substantially impermeable to moisture, and a sealing means arranged to close the at least one dispensing aperture, wherein the sealing means comprises a planar support having an opening or recess within which the container is received such that the planar support overlies and closes the at least one dispensing aperture.

32. A package as claimed in claim 31, wherein the planar support comprises a sheet of plastics material, the sheet having an opening within which the container is received, the circumference of said opening being constituted by a ring of elastomeric material, said ring bearing upon said container so as to close said at least one dispensing aperture.

33. A cylindrical or substantially cylindrical container, the diameter of the container being greater than its depth, the container being formed from first and second cooperating components, wherein said first cooperating component is of generally cylindrical construction and has an open end, said second cooperating component fitting closely within or about the open end of the first cooperating component, and the container having contents consisting essentially of a single unit dose of a powdered inhalation medicament.

34. A container as claimed in claim 33, wherein the container is provided with at least one dispensing aperture.

35. A container as claimed in claim 34, wherein the dispensing aperture is closed by a removable sealing means.

36. A system for the administration of a powdered medicament by inhalation, the system comprising a container containing a unit dose of medicament in powder form, the container having at least one dispensing aperture and the container being formed from first and second cooperating components, and a device having a chamber adapted to receive said container, the device further comprising air inlet means by which air may be drawn into the chamber and a mouthpiece by which air and entrained medicament may be drawn out of the chamber, wherein the chamber is substantially circular or annular in form and, in use, the container follows an orbital path within the chamber, and wherein the air inlet means open into a peripheral wall of the chamber, which peripheral wall has a height, but said air inlet means have a depth which is less than said height so that at least part of said peripheral wall forms an uninterrupted annular surface.

37. A system as claimed in claim 36, wherein the air inlet means are arranged such that air enters the chamber substantially tangentially so as to facilitate orbital motion of the container within the chamber.

38. A system as claimed in claim 36, wherein the chamber is provided with a formation which serves to constrain the movement of the container in its orbital path.

39. A system as claimed in claim 38, wherein said formation is a protrusion in the centre of the chamber.

40. A system as claimed in claim 36, wherein air passes out of the chamber to the mouthpiece through a mesh or grid formed in part of a wall of the chamber.

41. A system as claimed in claim 40, wherein the mesh or grid is formed in a base of the chamber and a radially outer part of the base is solid.

42. A system as claimed in claim 36, wherein the mouthpiece is formed at the open end of a passageway or conduit which connects the chamber to the mouthpiece and the passageway or conduit is disposed substantially orthogonally to an axis of rotation of the container in the chamber.

43. A system as claimed in claim 36, wherein the device is configured for repeated use, and means are provided for introducing a container into the chamber and removing the container after use.

44. A system as claimed in claim 36, which is for single dose use and is supplied with a container of medicament incorporated into the device in such a way that the dispensing aperture is sealed, the container being released from the device, and the dispensing aperture thereby opened, by the patient immediately before use.

45. A system as claimed in claim 36, wherein the container is cylindrical or substantially cylindrical.

46. A system as claimed in claim 45, wherein the diameter of the container is greater than its depth.

47. A system as claimed in claim 36, wherein said first cooperating component is of generally cylindrical construction and has an open end, said second cooperating component fitting closely within or about the open end of the first cooperating component.

48. A system as claimed in any claim 36, wherein the container is provided with a plurality of dispensing apertures.

49. A system as claimed in any claim 36, wherein the container is of a material which is substantially impermeable to moisture.

50. A system as claimed in claim 36, wherein the container is formed at least in part from metal sheet.

51. A system as claimed in claim 50, wherein the metal sheet is aluminium sheet.

52. A system as claimed in claim 36, wherein the motion of the container, in use, is epicyclic.

* * * * *